(12) United States Patent
Niebuhr et al.

(10) Patent No.: US 11,672,924 B2
(45) Date of Patent: Jun. 13, 2023

(54) INHALER, IN PARTICULAR AN ELECTRONIC CIGARETTE PRODUCT

(71) Applicant: KÖRBER TECHNOLOGIES GMBH, Hamburg (DE)

(72) Inventors: Gunnar Niebuhr, Hamburg (DE); Rene Schmidt, Buchholz I.D.N. (DE); Marc Kessler, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 324 days.

(21) Appl. No.: 16/755,707

(22) PCT Filed: Oct. 11, 2018

(86) PCT No.: PCT/EP2018/077728
§ 371 (c)(1),
(2) Date: Apr. 13, 2020

(87) PCT Pub. No.: WO2019/072966
PCT Pub. Date: Apr. 18, 2019

(65) Prior Publication Data
US 2021/0195951 A1    Jul. 1, 2021

(30) Foreign Application Priority Data
Oct. 13, 2017    (DE) .......................... 102017123866.2

(51) Int. Cl.
*A24F 13/00* (2006.01)
*A61M 11/04* (2006.01)
(Continued)

(52) U.S. Cl.
CPC ............. *A61M 11/042* (2014.02); *A24F 7/00* (2013.01); *A24F 40/30* (2020.01); *A24F 40/42* (2020.01);
(Continued)

(58) Field of Classification Search
CPC ....................................................... A24F 47/00
(Continued)

(56) References Cited

U.S. PATENT DOCUMENTS 4,532,530 A    7/1985    Hawkins
5,505,214 A    4/1996    Collins et al.
(Continued)

FOREIGN PATENT DOCUMENTS

DE    20 2013 010 238 U1    4/2014
DE    10 2016 002 665 A1    3/2016
(Continued)

OTHER PUBLICATIONS

1st Examination Report issued by the German Patent and Trademark Office with respect to the priority German Patent Application No. 10 2017 123 866.2.
(Continued)

*Primary Examiner* — Phuong K Dinh
(74) *Attorney, Agent, or Firm* — Saliwanchik, Lloyd & Eisenschenk (57) ABSTRACT

The invention relates to an inhaler, in particular an electronic cigarette product, comprising at least one evaporator unit with at least one electric evaporator for evaporating liquid supplied to the evaporator and comprising an electronic controller for controlling and/or regulating the at least one evaporator unit. The inhaler has at least one replaceable cartridge, wherein the cartridge has the evaporator unit and a liquid tank which is connected or can be connected to the evaporator unit.

18 Claims, 6 Drawing Sheets

(51) Int. Cl.
*A24F 40/30* (2020.01)
*A24F 40/60* (2020.01)
*A24F 40/90* (2020.01)
*A24F 40/42* (2020.01)
*A24F 40/50* (2020.01)
*A24F 7/00* (2006.01)
*A24F 40/10* (2020.01)
*A24F 40/40* (2020.01)

(52) U.S. Cl.
CPC .............. *A24F 40/50* (2020.01); *A24F 40/60* (2020.01); *A24F 40/90* (2020.01); *A24F 40/10* (2020.01); *A24F 40/40* (2020.01)

(58) Field of Classification Search
USPC .................................................. 131/328–329
See application file for complete search history.

(56) References Cited

U.S. PATENT DOCUMENTS

| | | | |
|---|---|---|---|
| 9,018,899 B2* | 4/2015 | Xiang | H02J 7/00309 320/108 |
| 9,936,735 B1* | 4/2018 | Shotey | A24F 40/60 |
| 10,299,514 B2* | 5/2019 | Bilat | A24F 40/57 |
| 2006/0196968 A1 | 9/2006 | Rabin et al. | |
| 2009/0224064 A1 | 9/2009 | Brodbeck et al. | |
| 2011/0277757 A1 | 11/2011 | Terry et al. | |
| 2013/0087160 A1 | 4/2013 | Gherghe | |
| 2013/0300350 A1 | 11/2013 | Xiang | |
| 2014/0060554 A1 | 3/2014 | Collett et al. | |
| 2014/0060556 A1 | 3/2014 | Liu | |
| 2014/0366898 A1 | 6/2014 | Monsees | |
| 2015/0027457 A1 | 1/2015 | Janardhan et al. | |
| 2015/0090280 A1 | 4/2015 | Chen | |
| 2015/0114407 A1 | 4/2015 | Duncan | |
| 2016/0219938 A1 | 8/2016 | Mamoun et al. | |
| 2016/0262454 A1 | 9/2016 | Sears et al. | |
| 2016/0345630 A1 | 12/2016 | Mironov et al. | |
| 2017/0163050 A1 | 6/2017 | Hwang et al. | |
| 2017/0167509 A1 | 6/2017 | Selig | |
| 2017/0188626 A1 | 7/2017 | Davis et al. | |
| 2017/0231282 A1 | 8/2017 | Christensen | |
| 2017/0251727 A1 | 9/2017 | Nielsen | |
| 2017/0258132 A1 | 9/2017 | Rostami et al. | |
| 2017/0258140 A1 | 9/2017 | Rostami et al. | |
| 2017/0290371 A1 | 10/2017 | Davis et al. | |
| 2017/0347708 A1 | 12/2017 | Shin | |
| 2019/0246696 A1 | 8/2019 | Schmidt et al. | |

FOREIGN PATENT DOCUMENTS

| | | |
|---|---|---|
| DE | 10 2015 107 082 A1 | 11/2016 |
| JP | 2014-504142 A | 2/2014 |
| WO | WO 2011/146174 A2 | 11/2011 |
| WO | WO 2014/066730 A1 | 2/2014 |
| WO | WO 2015/038981 A2 | 3/2015 |
| WO | WO 2015/076515 A1 | 5/2015 |
| WO | WO 2015/128667 A1 | 9/2015 |
| WO | WO 2016/090426 A1 | 6/2016 |
| WO | WO 2016/099045 A1 | 6/2016 |
| WO | WO 2016/177604 A1 | 11/2016 |
| WO | WO 2017/093535 A1 | 6/2017 |
| WO | WO 2017/163050 A1 | 9/2017 |
| WO | WO 2017/167509 A1 | 10/2017 |
| WO | WO 2018/083007 A1 | 5/2018 |

OTHER PUBLICATIONS

Office Action issued by the Japanese Patent Office dated Nov. 21, 2022 in parallel Japanese Application No. 2020-520575.
Appeal Issued by G.D. S.p.A dated Feb. 10, 2023 for parallel European patent No. 3 694 350.

* cited by examiner

INHALER, IN PARTICULAR AN ELECTRONIC CIGARETTE PRODUCT

CROSS REFERENCE TO RELATED APPLICATIONS

This application is a National Stage Application of International Application Number PCT/EP2018/077728, filed Oct. 11, 2018; which claims priority to German Patent Application No. 10 2017 123 866.2, filed Oct. 13, 2017.

FIELD OF INVENTION

The present invention relates to an inhaler, in particular an electronic cigarette product, comprising at least one evaporator unit with at least one electric evaporator for evaporating liquid supplied to the evaporator and comprising an electronic controller for controlling and/or regulating the at least one evaporator unit.

BACKGROUND OF THE INVENTION

Current electronic cigarettes use between one and up to five evaporator heads based on the wick-spiral principle, which heads draw their liquid from a common reservoir. The consumer can only adjust the total output of the evaporation device and thereby the amount of vapour produced; further adjustments are not possible.

BRIEF SUMMARY OF THE INVENTION

The object of the invention is to provide an inhaler offering a higher degree of comfort, a variety of functionalities and/or an improved customisation of the smoking experience.

The invention achieves this object with the features of independent claim 1. According to the invention, the inhaler has at least one replaceable cartridge which comprises the evaporator unit and a liquid tank which is connected or can be connected. Due to the replaceable cartridge, the consumer can insert and consume the desired liquid in the inhaler in a simple manner and as desired, i.e. with the desired taste and/or the desired active ingredient content and/or vapour generation potential.

The cartridge preferably forms a plurality of reservoirs for storing a plurality of liquids. By holding a plurality of liquids in the inhaler, a desired smoking experience can be achieved by selecting the liquid that is currently to be evaporated without having to change the cartridge. For example, if one reservoir has nicotine and one reservoir has a flavour, the nicotine effect and flavour effect can be controlled independently of one another, which is not possible with conventional single-chamber systems. Different and changeable flavour combinations are also possible.

For the above purpose, the inhaler advantageously has a selection element which can be actuated by the consumer, for selecting a reservoir, from which liquid is to be evaporated, from the plurality of reservoirs. In a simple and intuitively operated embodiment, the selection element is a push button, the plurality of reservoirs being sequentially run through by repeated actuation of the push button. Other embodiments of the selection element are possible, for example in the form of a slide switch.

In the variant described above, the inhaler can preferably have an in particular optical indicator, which informs the consumer about the selected reservoir and/or about the liquid contained therein. In particular, this indicator can display a characteristic of the selected liquid, in particular taste, active ingredient content and/or vapour formation potential. This can happen for example by means of colour coding or in another suitable way.

In an advantageous embodiment of the invention, the inhaler has a head in which all the cartridges and advantageously also the energy store of the inhaler are arranged entirely or in part. In this embodiment, the weight of the inhaler is concentrated in the head. The head advantageously forms a handle for the consumer, such that the inhaler can be comfortably held by a one-handed grip on the head and brought to the mouth in the manner of a conventional tobacco pipe. This results in a particularly advantageous manageability of the inhaler.

In the embodiment described above, the inhaler has a puff tube that connects a mouthpiece of the inhaler to the aforementioned head. The puff tube is used to homogenise the air/vapour/aerosol mixture in order to produce the most constant active ingredient/flavour administration and, if necessary, to cool down hot vapours or gases. For this purpose, the length of the puff tube is advantageously greater than the length of the head, which further improves the manageability of the inhaler.

The inhaler preferably has a reversibly removable cover for closing an opening in a housing of the inhaler, through which opening the cartridge can be inserted into the inhaler and removed therefrom. The cover can advantageously be reusable. The cover is advantageously held on the housing of the inhaler by means of at least one magnetic element, which simplifies the removal of the cover for changing the cartridge. Other connection elements can also be considered, such as clip connections.

In a preferred embodiment, the cover has at least one number of cartridge receptacles corresponding to the number of cartridges that can be inserted into the inhaler. Each receptacle then has at least one electrical contact element for interacting with a corresponding electrical contact element of the cartridge to be inserted into the receptacle.

Inserting the cartridges into the cover can be made easier and more convenient for the consumer than inserting them into a base part of the inhaler. However, the latter variant is not excluded. In the embodiment described above, the cover advantageously has an electrical contact means which is connected to the electrical contact element for the cartridge and is set up to interact with a corresponding contact means arranged on a base part of the inhaler in order to establish an electrical connection between the at least one cartridge and the base part.

Incomplete insertion of cartridges advantageously does not affect the functionality of the inhaler. However, an incomplete insertion of cartridges can advantageously be recognised and, depending on the application, for example in medical use, can lead to blocking of the inhaler operation. A similar procedure can also be followed if one of the cartridges is emptied prematurely. It would also be possible to ensure uniform emptying of the cartridges by restricting the removal from one or more cartridges, preferably with prior notification of the user.

The inhaler preferably has a switch for setting different operating variables of the inhaler. In particular, the switch can be set up to set the amount of vapour to be generated per puff, which has the advantage that the consumer can set a desired amount of vapour simply and quickly. As an alternative or in addition, the switch can be set up to adjust the puff resistance of the inhaler. Finally, the switch can alternatively or additionally also serve as an on-off switch for the inhaler. Accordingly, the switch can perform a plurality of functions, so that corresponding separate switches for carrying out individual functions are unnecessary, which reduces the manufacturing outlay and simplifies the operation of the inhaler.

The inhaler preferably has an inductive charging interface for inductively charging the energy store. Such wireless charging is less susceptible than wired charging, for example via a USB interface, but this is not excluded.

The inhaler advantageously has an actuating element for triggering a briefly increased amount of vapour and/or active ingredient by the consumer, i.e. an evaporation boost. This makes it possible in a simple manner to release a particularly large amount of vapour in a short time for a sudden nicotine and/or taste effect (kick) desired by the consumer.

In one embodiment of the invention, a mouthpiece of the inhaler can be adjusted, in particular displaceably, by means of an actuating element between a position lowered into the inhaler housing and an extended operating position. This allows an effective, hygienic protection of the mouthpiece in the lowered position when the inhaler is not in use. A separate protective cap for the mouthpiece, which can easily be lost, is then unnecessary.

Particularly advantageously, the inhaler can be switched off by moving the mouthpiece into the lowered position and the inhaler can be switched on by moving the mouthpiece into the extended position. The described actuating element then simultaneously serves as an on-off switch of the inhaler, such that a separate on-off switch is unnecessary.

Further advantageously, the puff resistance of the inhaler can be changed by adjusting the mouthpiece. In this case, a separate actuating element for adjusting the puff resistance may be unnecessary.

BRIEF DESCRIPTION OF THE FIGURES

The invention will be explained below on the basis of the preferred embodiments with reference to the accompanying drawings. In the drawings.

DETAILED DESCRIPTION

The inhaler 27 comprises an evaporator device 1 for evaporating one or more liquids from one or more liquid tanks 6, and an advantageously reusable base part 20. An advantageous construction of the inhaler 27 and in particular of the evaporator device 1 can be seen by way of example in FIGS. 1, 2, 8 and 9.

The evaporator device 1 advantageously comprises one or more evaporator units 23. Each evaporator unit 23 advantageously comprises a carrier 2, which can be designed as a carrier plate and to which a liquid tank 6 is connected or can be connected. Each evaporator unit 23 has one evaporator 3 (FIG. 2) or a plurality of evaporators 3 (FIG. 1) which are used to evaporate liquid supplied to the evaporator(s) 3 from the liquid tank 6 and which are advantageously mounted on the carrier 2. The advantageously continuous, dimensionally stable carrier 2 can consist of a suitable, advantageously non-conductive material, for example ceramic or a suitable plastics material, in particular PEEK, or fibre-reinforced plastic, for example PCB material.

Figure 1:
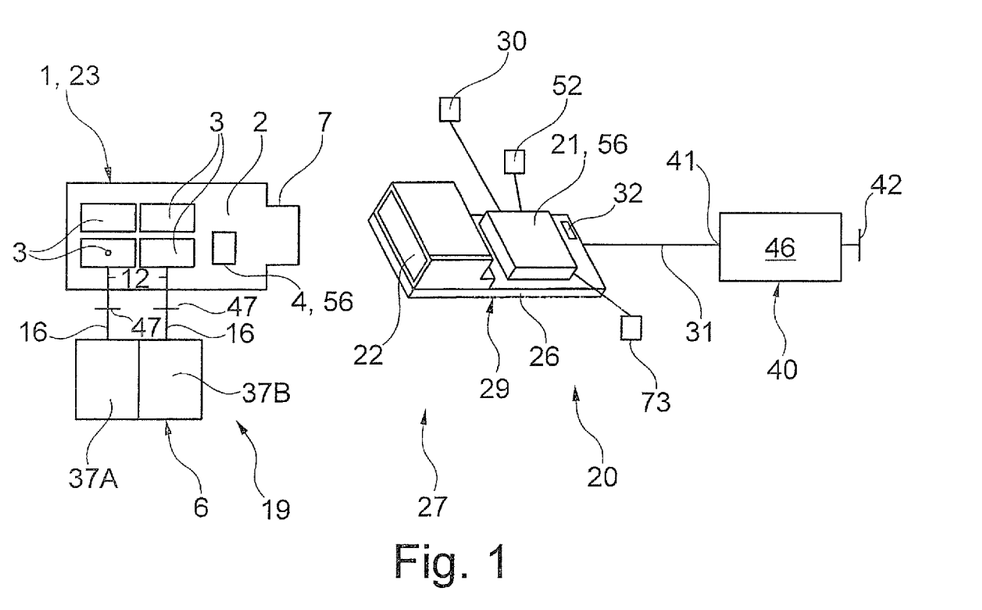
FIG. 1 is a schematic representation of an e-cigarette in one embodiment of the invention.
Figure 2:
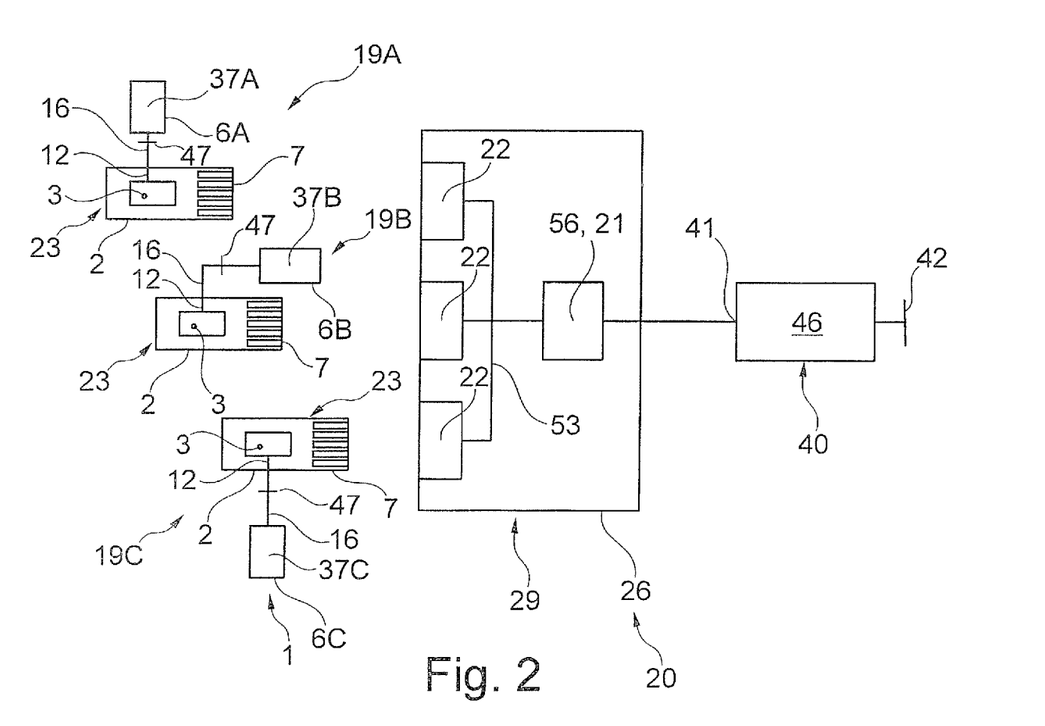
FIG. 2 is a schematic representation of a further e-cigarette in a further embodiment of the invention.

In the embodiment according to FIG. 1, the evaporators 3 are arranged, for example, in matrix form, here for example four evaporators 3 in 2×2 matrix form.

The liquid supplied to the evaporator 3 is converted into vapour/aerosol by the evaporator 3. The in particular electric evaporator 3 has at least one, preferably a plurality of electrical resistance heating elements 15, see FIG. 9.

Each evaporator unit 23 is advantageously embodied in a structural unit having a liquid tank 6 as a replaceable cartridge 19. Each cartridge 19 advantageously has a cartridge housing 63 which can be formed at least partially by the liquid tank 6 and/or at least partially by the evaporator unit 23. The at least one liquid tank 6 can be refillable, so that the cartridge 19 is a reusable part. The cartridge 19 can alternatively be designed as a disposable part.

Each evaporator unit 23 or each cartridge expediently has a vapour outlet opening 64, through which generated vapour and/or aerosol can escape from the evaporator unit 23 and can be mixed with the air flowing through the inhaler, in order to be inhaled by the consumer after escaping from the inhaler 27 through the puff opening 24.

Each evaporator unit 23 advantageously comprises a digital electronic control device 4, for example an application-specific integrated circuit (ASIC), which can preferably be arranged on the carrier 2. The evaporator(s) 3 of the evaporator unit 23 can be controlled individually or in groups by the corresponding electronic control device 4 and heated by electricity from an energy store 46 in order to evaporate any liquid present on the heating elements 15.

The evaporator unit 23 or the cartridge 19 has an electrical contact element 7, here in the form of an electrical plug, having a plurality of electrical contacts 10. The contacts 10 are connected to the electronic control device 4 by means of electrical lines in order to transmit sensor signals, control signals and/or electrical energy to the base part 20 of the inhaler 27. The evaporator unit 23 can have sensors, for example a temperature sensor for measuring the heating temperature and/or a pressure sensor for measuring the flow pressure.

The base part 20 comprises a control unit 29 and an energy storage unit 40 connected or to be connected to the control unit 29. The control unit 29 comprises an electronic controller 21 and an electrical contact element 22 connected thereto, here in the form of a socket matching the plug 7. The control unit 29 advantageously further comprises a user interface 32, in particular a wireless interface, for example a Bluetooth interface, via which a user can control or adjust the inhaler 27 by means of a mobile communication device, for example a smartphone, and/or receive information therefrom. The electronic controller 21 and the electrical contact element 22 are advantageously arranged on a common circuit board 26. The entirety of electronic control device 4 and electronic controller 21 is referred to in the context of this application as an electronic control device 56 of the inhaler 27.

The electrical plug 7 and the electrical contact element 22 in the form of an electrical socket 22 are set up correspondingly with respect to one another, so that by plugging the plug 7 into the socket an electrical connection is established between the evaporator unit 23 and the base part 20 for the transmission of signals, data and/or electrical power. In the evaporator unit 23, the supply currents and signals from the plug 7 are forwarded to the at least one evaporator 3 and/or to sensors. The plug 7 and the electrical contact element 22 in the form of an electrical socket advantageously each have the same number of electrical contacts 10.

Figure 7:
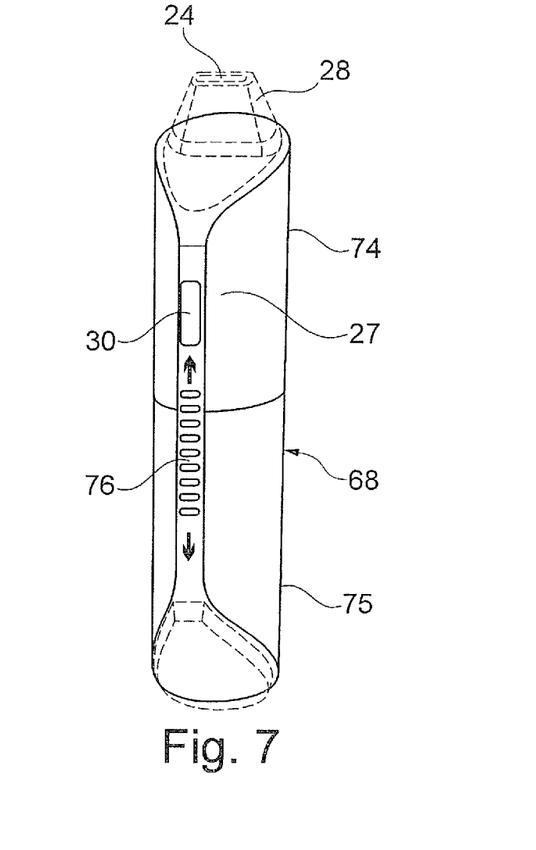
FIG. 7 is a perspective view of a rod-shaped electronic cigarette product.
Figure 8:
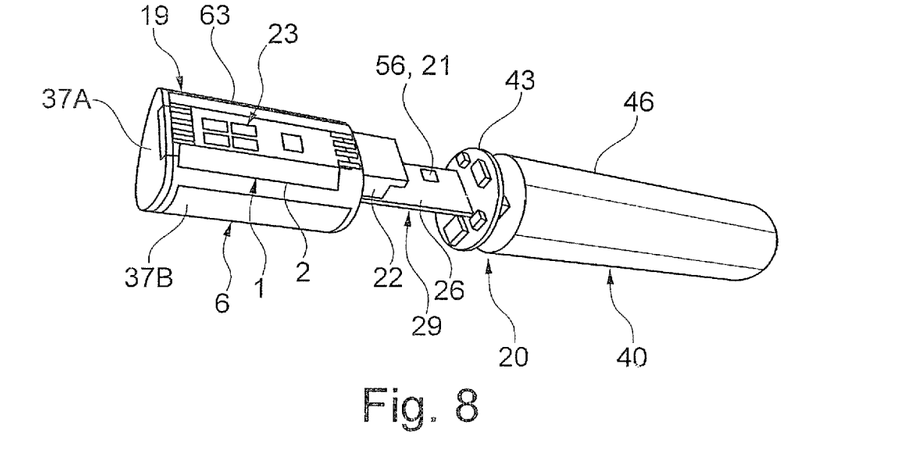
FIG. 8 is a perspective view of the interior of the electronic cigarette product according to FIG. 7.

To connect the evaporator unit 23 to the base part 20, in some embodiments, for example according to FIGS. 7 and 8, the cartridge 19 is pushed into the base part 20 parallel to the longitudinal axis thereof, as a result of which the plug 7 is pushed into the electrical contact element 22 in the form of an electrical socket and the electrical connection is established.

Advantageously, the base part 20 or the control unit 29 has a number of electrical contact elements 22, here plug sockets, corresponding to the number of cartridges 19, in order to allow the individual exchange of single cartridges 19. The electrical contact elements 22 in the form of electrical sockets are connected to the electronic controller 21 of the base part 20 by means of a manifold 53.

An identifier (ID) of the evaporator unit 23 is advantageously permanently stored in the electronic control device 4 of the evaporator unit 23. As a result of the connection of the cartridge 19 to the base part 20, the electronic controller 21 can read out the identifier from the control device 4 and carry out or initiate an individual control of the respective evaporator 3 and/or the respective evaporator unit 23 that is specific to the type and optimised with regard to the respective liquid, for example by transmitting control and/or regulation commands to the control device 4. Control data for a plurality of identifiers corresponding to a plurality of different evaporators 3 or evaporator types and/or liquids are preferably stored in the electronic controller 21 of the base part 20 for this purpose, for example in the form of a database.

The energy storage unit 40 comprises an energy store 46, a battery interface 41 for connecting the control unit 29 to the energy storage unit 40 via electrical lines 31, a charging interface 42, and an electronic circuit 43 having charging electronics. The control unit 29 is supplied with current via the battery interface 41. Furthermore, analogue and/or digital signals can be transmitted between the energy storage unit 40 and the control unit 29 via the battery interface 41. In an advantageous embodiment, the electrical lines 31 comprise a digital data bus. The electrical connection 31 between the base part 20 and the energy storage unit 40 can be used, for example, to transmit information about the state of charge of the energy store 46 or diagnostic data between the control unit 29 and the energy storage unit 40. The energy store 46 can be a disposable battery or a rechargeable battery, for example a lithium-ion battery, which can be charged via the charging interface 42, for example a USB interface, or advantageously wirelessly via an inductive charging interface.

Each evaporator unit 23 advantageously has a standardised liquid interface 47 for connecting the liquid tank 6 to the evaporator unit 23, in particular the carrier 2 thereof. The liquid interface 47 is advantageously arranged on the side of the carrier 2 opposite the evaporator 3. Accordingly, the liquid from the reservoir(s) 37A, 37B is provided at the liquid interface 47 and is passed through an advantageous passage opening through the carrier 2 to the evaporator(s) 3. The liquid interface 47 can be sealed, for example, by means of a sealing element. The tank 6 can be detachably or non-detachably connected to the corresponding evaporator unit 23 for the consumer.

The liquid tank or each liquid tank 6 forms a respective liquid reservoir 37A, 37B, 37C (embodiment according to FIGS. 2 to 6) or a plurality of liquid reservoirs 37A, 37B (embodiments according to FIGS. 1, 7 to 9). In particular, a multi-chamber tank 6 can be provided to form a plurality of reservoirs 37A, 37B, . . . By way of example, a cartridge 19 having a two-chamber tank 6 is provided in each case in FIGS. 1 and 7 to 9, in order to form two reservoirs 37A, 37B. Of course, a liquid tank 6 can also form more than two reservoirs 37A, 37B. In the embodiment according to FIG. 1, two evaporators 3 are in each case assigned to a reservoir 37A, 37B by way of example. Of course, only one evaporator 3 (see FIG. 2) or more than two evaporators 3 can be assigned to a reservoir 37A, 37B.

In the embodiments according to FIGS. 2 to 6, the reservoirs 37A, 37B, 37C are realised by means of single-chamber tanks 6A, 6B, 6C. That is, each tank 6A, 6B, 6C has only one chamber for forming a reservoir 37A, 37B, 37C. In the embodiment according to FIG. 2, for example, three cartridges 19, each having an evaporator unit 23 and having a single-chamber tank 6A, 6B, 6C, are provided. The number of cartridges 19 or tanks 6 can also be one, two or more than three. Embodiments having an individual single-chamber tank 6 are included.

Mixed forms between single and multi-chamber tanks are possible, for example a two-chamber tank and a single-chamber tank could be provided in FIGS. 2 to 6.

Each liquid reservoir 37A, 37B, . . . is connected to one or more evaporators 3 via an associated liquid feed 16 in order to transport liquid from a corresponding opening 58 in the liquid tank 6 to the evaporator(s) 3, where it is evaporated. The liquid feeds 16 can comprise, for example, passage bores in an intermediate part 57 between the carrier 2 and the liquid tank 6, see FIG. 9.

A capillary element 12 is advantageously provided between each evaporator 3 and the associated liquid reservoir 37A, 37B, . . . , i.e. in the liquid feed 16, and conveys liquid from the liquid tank 6 to the evaporator 3 by means of capillary action, for example with the aid of microchannels, in order to ensure the wetting of the evaporator 3 and the continuous replenishment of liquid. The capillary element 12 can comprise, for example, a pore element having an optimised pore size, an open-pore foamed element, a sponge element and/or a lamellar structure.

The evaporator(s) 3 can be designed according to need and expediency. For example, evaporators 3 having line channels or microchannels can be used, as described in DE 10 2016 120 803.5, the disclosure content of which is included in the present application. This variant is explained in more detail with reference to FIG. 12. Bionic heating structures, such as bionic networks, are also possible for the evaporator 3. Evaporators 3 having heating structures as described in DE 10 2017 111 119.0 are also possible, the disclosure content of which is included in the present application.

A preferred embodiment of the inhaler 27 in the form of a conventional tobacco pipe is explained below with reference to FIGS. 3 to 6. The inhaler 27 is elongated overall and has a mouthpiece 28 having a puff opening 24 for the consumer at the proximal end, i.e. at the puff end. At the distal end opposite the mouthpiece 28, the inhaler 27 has a head 25. Between the mouthpiece 28 and the head 25, there is a stem or puff tube 59 which connects the mouthpiece 28 to the head 25.

Figure 3:
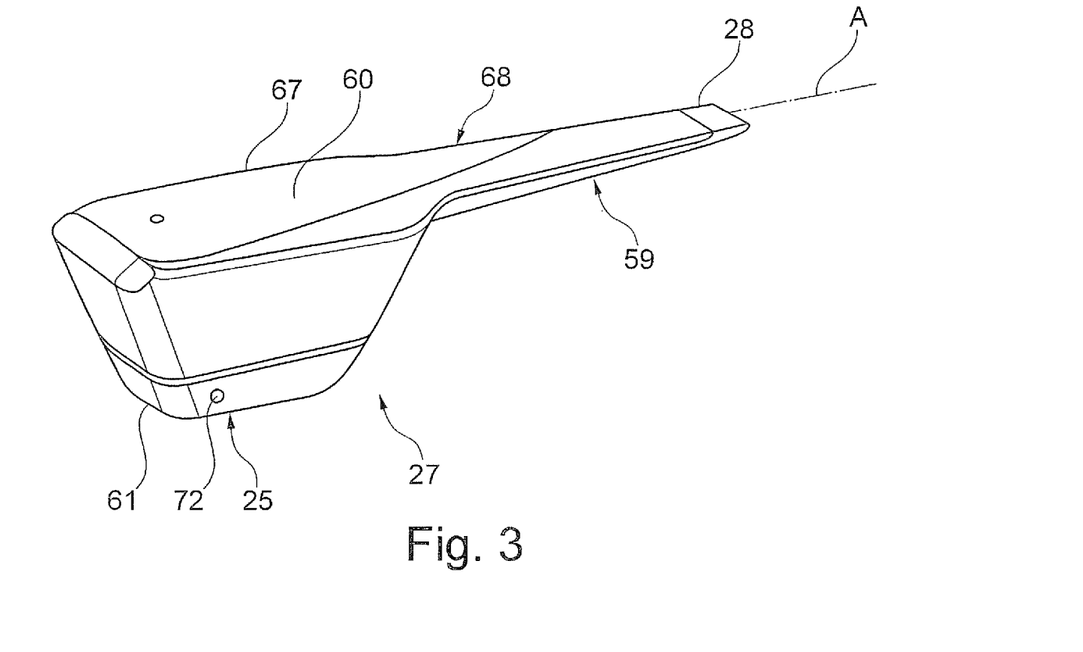
FIG. 3 is a perspective view obliquely from above of a pipe-shaped electronic cigarette product.
Figure 4:
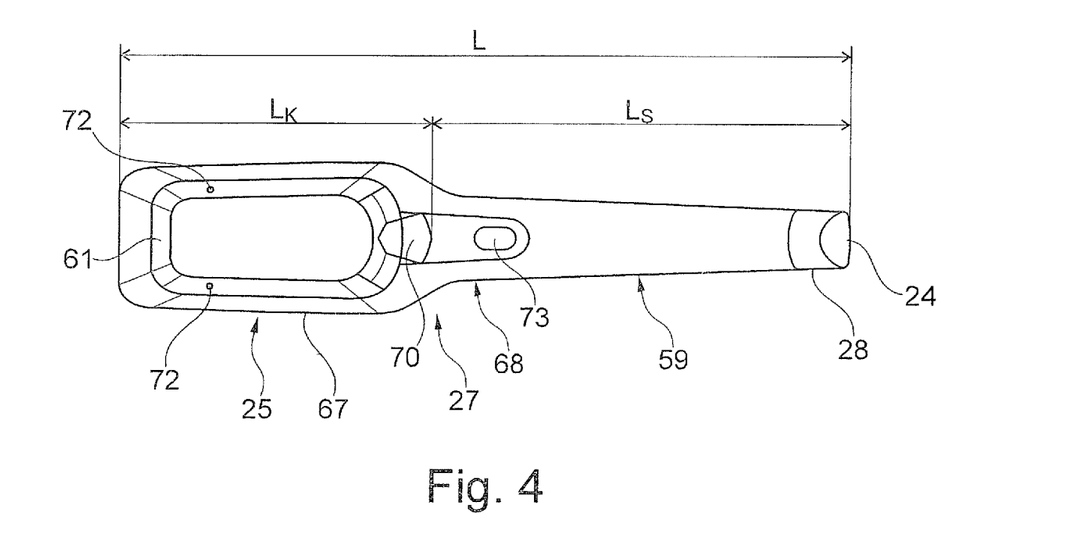
FIG. 4 is a view from below of the electronic cigarette product according to FIG. 3.
Figure 5:
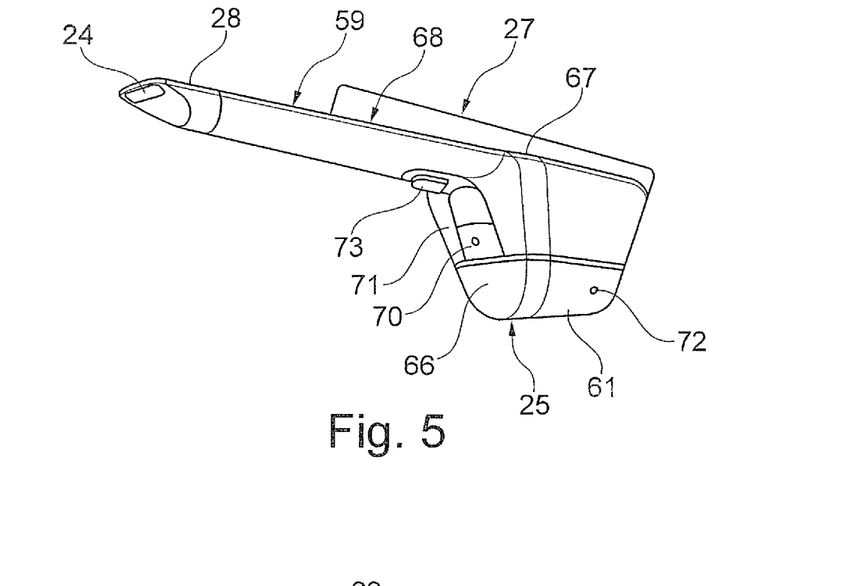
FIG. 5 is a perspective view obliquely from below of the electronic cigarette product according to FIGS. 3 and 4.
Figure 6:
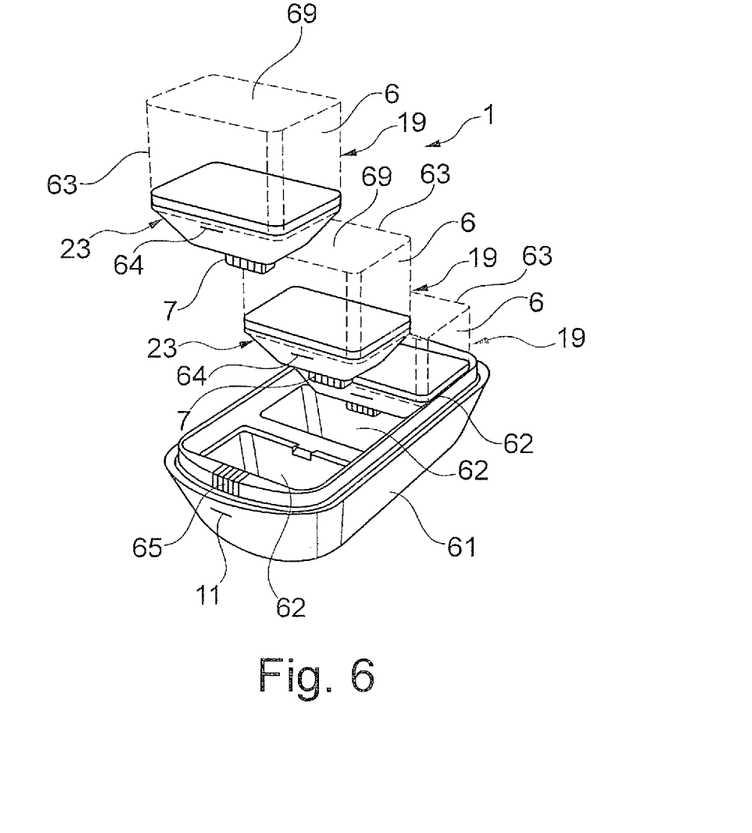
FIG. 6 is a perspective view obliquely from above of a part of the electronic cigarette product according to FIGS. 3 to 5.

The head 25 extends transversely to the longitudinal axis A of the puff tube 59 substantially in one direction, namely downwards, as can be seen for example in FIGS. 3 and 5. Accordingly, the puff tube 59 and the head 25 form a continuous upper side 60 of the inhaler. The head 25 preferably tapers downwards, i.e. with increasing distance from the tube axis A.

The length Lk of the head 25 is preferably less than half the length L of the inhaler 27. The length of the puff tube 59 is preferably more than half the length L of the inhaler 27. The length Lk of the head 25 is thus advantageously less than the length Ls of the puff tube 59, which improves the manageability of the inhaler 27.

The inhaler 27 comprises a housing 68 which advantageously comprises two housing parts 61, 67 which can be reversibly connected to one another by the consumer, namely a housing base part 67 for the majority of the inhaler 27, and a cover 61 for reversibly closing an insertion opening in the head 25 which is removable by the consumer in order to be able to remove cartridges 19 from the inhaler 27 and to insert them into said inhaler. The cover 61 is designed here as a trough, which closes the head 25 on the underside thereof. The cover 61 can alternatively be arranged on the top 60 of the head 25 or at another suitable location of the head 25.

The cover 61 is advantageously held by means magnets on the housing base part 67 and thus on the inhaler 27, which is particularly easy for the consumer to handle. Alternative fastenings are possible, for example positive fastening, such as by means of clip elements.

The evaporator device 1 is preferably arranged entirely or substantially entirely in the head 25 of the inhaler 27. In particular, the cartridges 19 are preferably arranged entirely in the head 25. In the embodiment of FIGS. 3 to 6, the cartridges 19 can be inserted into the cover 61. This can be seen in FIG. 6. For this purpose, the cover 61 has receptacles 62 for the cartridges 19, a cartridge 19 being insertable into each receptacle 62.

The electrical contact elements 22 for interacting with the corresponding electrical contact elements 7 of the cartridges 19 are expediently arranged in the receptacles 62, in particular at the base thereof. All the electrical contact elements 22 are connected to an electrical contact means 65 by means of a manifold 53 (see FIG. 2). A corresponding electrical contact means (not shown) is arranged in the interior of the head 25. When the cover 61 is connected to the head 25, the electrical contact means 65 is brought into contact with the corresponding electrical contact means in the head 25 in order to establish the electrical connection between the evaporator units 23 and the base part 20. The contact means 65 thus serves for communication between the cartridges 19 and the base part 20.

In an alternative embodiment, the receptacles 62 for the cartridges 19 are provided in the head 25 instead of in the cover 61, i.e. the cartridges 19 can be inserted directly into the head 25. In this case, the cover 61 serves substantially only to close the insertion opening in the head 25. The contact means 65 can then be dispensed with, the manifold 53 is optionally arranged in the head.

At least one, for example, slot-shaped air inlet opening 66 is provided in the housing 68 of the inhaler 27. The air inlet opening 66 is advantageously arranged on the head 25 and further advantageously in the cover 61, see FIG. 6. The puff tube 59 has a continuous air channel in its interior. When the consumer creates a negative pressure in the inhaler 27 by puffing on the mouthpiece 28 or the puff opening 24, ambient air enters the inhaler through the air inlet opening 11 and passes through the head 25 and the puff tube 59 until it escapes from the puff opening 24. As described above, this air flow through the evaporator device 1 is admixed with vapour/aerosol. The puff tube 59 is used to homogenise the air/vapour/aerosol mixture in order to produce the most consistent active ingredient/flavour administration possible and, if necessary, to cool down hot vapours or gases.

In the following, without restricting the generality, the case is considered that a plurality of liquid reservoirs 37A, 37B, . . . are provided for the inhaler 27. Liquid reservoirs 37A, 37B, . . . can contain different liquids A, B, C and/or the same liquids. The liquid(s) in the reservoirs 37A, 37B, . . . advantageously comprise one or more components from the group 1,2-propylene glycol, glycerol, water, at least one active ingredient, in particular nicotine, and/or at least one flavouring agent (flavour) in the same and/or different mixing ratios.

By using several reservoirs 37A, 37B, . . . and a plurality of corresponding liquid feeds 16, the evaporator(s) 3 can evaporate different liquids having different compositions contained in the reservoirs 37A, 37B, . . . . In this way, the composition of the vapour or aerosol produced by the evaporator(s) 3 can be adjusted in a targeted manner. Furthermore, the vapour/aerosol composition can be modified in a targeted manner by targeted evaporation of different liquids.

By way of example, the nicotine content can be set or changed by the consumer if cartridges 19 having a liquid A with nicotine and a liquid B without nicotine are inserted into the inhaler 27. Furthermore, the taste experience can be set or changed by the consumer when cartridges 19 having a liquid C with a flavour C and a liquid D without flavour C or with another flavour D are inserted into the inhaler 27.

Depending on the liquid or liquid composition contained therein, the cartridges 19 can be coded such that they can be recognised by the consumer. For example, the cartridges 19 can be colour-coded, for example on the upper side 69 of the cartridge housing 63 opposite the connector 7. Other optical codes, for example by means of graphical icons and/or alphanumerical labelling are possible. Because of the coding, the consumer can easily and correctly recognise different flavours, active substance contents and/or vapour generation potential of individual cartridges 19 and insert them into the inhaler 27 as desired.

The consumer can advantageously select individual cartridges 19 (FIGS. 2 to 6) or individual reservoirs 37A, 37B, . . . (FIGS. 1, 7 to 9) from which liquid is to be evaporated. For this purpose, the housing 68 of the inhaler, advantageously the housing part 67 of the base part 20, has a corresponding selection element or setting element 70, see FIG. 5. The selection element 70 can be arranged particularly advantageously on the head 25, in particular in a surface 71 facing the puff opening 24 below the puff tube 59.

In an advantageous embodiment, the selection element or setting element 70 is a push button. By repeatedly pressing the push button, all the reservoirs 37A, 37B, . . . are then run through sequentially. In the case of three reservoirs 37A, 37B, 37C, repeated actuation of the push button would select the reservoir from which liquid is to be evaporated, according to the following sequence: 37A, 37B, 37C, 37A, 37B,

37C, 37A, . . . etc. The push button 70 thus serves to sequentially change all the reservoirs 37A, 37B, . . . and the liquids contained therein.

The selection element 70 need not be a push button, for example it can alternatively be a switch, for example a slide switch, preferably having a number of switch positions corresponding to the number of selectable reservoirs 37A, 37B, . . . . Other designs of the selection element 70 are possible.

As a result of the selection of a reservoir 37A, 37B, . . . by means of the selection element 70, the selected reservoir is (only) used for the supply of liquid during the next evaporation, i.e. the next puff by the consumer. This can be done in particular by individually triggering the evaporator unit 23 or evaporator 3 assigned to the selected reservoir 23. For this purpose, the evaporator units 23 or evaporators 3 individually assigned to the reservoirs 37A, 37B, . . . can be individually triggered.

The inhaler 27 advantageously has an optical indicator 72, in particular, which informs the consumer about the selected reservoir 37A, 37B, . . . and/or about the selected liquid. The optical indicator 72 is advantageously arranged on the cover 61, but can also be arranged on the housing base part 67. The optical indicator 72 may include, for example, one or more LEDs, LCDs, or other suitable electronic indicator elements. In the present example, the indicator 72 comprises two LEDs, namely one LED on each side of the head 25. The number of LEDs can be more or less than two.

The optical indicator 72 is in particular set up to display the characteristic of the selected liquid, in particular the flavour, active ingredient content and/or vapour formation potential. This can happen, for example, by changing the colour of the optical indicator 72 or the LEDs, or in some other way, for example by displaying graphical icons and/or alphanumerical indicators.

The inhaler 27 preferably comprises a switch 73 for setting different operating variables of the inhaler 27. In particular, the switch 73 can be used to adjust the amount of vapour to be generated per puff, the puff resistance of the inhaler 27 and/or as an on-off switch for the inhaler 27. Accordingly, the switch 73 advantageously comprises a zero position in which the inhaler 27 is switched off, i.e. the power supply through the energy store 46 is interrupted.

Furthermore, the switch 73 comprises at least one further position in which the inhaler 27 is switched on. Preferably, two or more additional on-positions of the switch 73 are provided, which differ in the different generation of vapour quantity and/or different puff resistances of the inhaler 27. For example, a first position can be provided in which less vapour is generated and a higher puff resistance of the inhaler 27 is set, and a second position in which more vapour is generated and a lower puff resistance of the inhaler 27 is set. Of course, three or more on-position switches 73 can be provided.

If, as described, the amount of vapour and the puff resistance can be changed at the same time with the switch 73, a reduced puff resistance is preferably set with increasing amount of vapour and vice versa. The switch 73 can alternatively only serve to adjust the amount of vapour to be generated (without influencing the puff resistance), or only to adjust the puff resistance of the inhaler 27 (without influencing the amount of vapour to be generated). Furthermore, an on-off switch which is independent of the switch 73 can be provided.

The puff resistance is generally set in the inhaler 27 by means of a controllable element 52 influencing the puff resistance and shown schematically in FIG. 1.

The switch 73 can be designed as a rotary switch or slide switch. Other suitable designs are possible. The switch 73 is advantageously arranged on the underside of the puff tube 59 at a short distance from the head 25. The switch 73 can be arranged at another suitable location on the inhaler 27.

According to the above, the consumer can use the selection element 70 and/or the switch 73 to flexibly set the desired amount of vapour, the amount of active ingredient, the desired flavour and/or the desired puff resistance.

Figure 9:
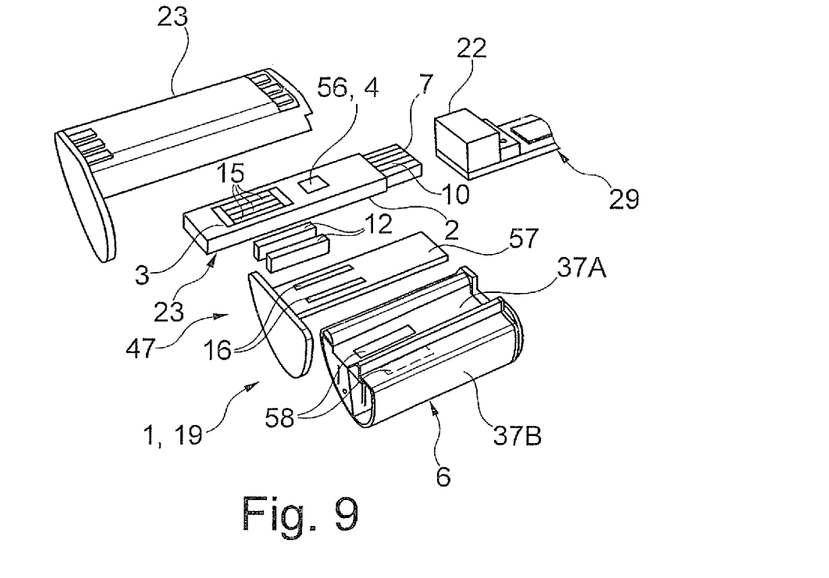
FIG. 9 is an exploded view of part of the electronic cigarette product according to FIGS. 7 and 8.

The embodiment according to FIGS. 7 to 9 relates to a substantially rod-shaped electronic cigarette product 27 having a cartridge 19 which forms a two-chamber tank 6 having two liquid stores 37A, 37B. The evaporators 3 assigned to the liquid stores 37A, 37B can be triggered independently of one another, such that the consumer can choose which liquid should be evaporated. In this way, the consumer can, for example, choose between a 100% nicotine experience (liquid A), a 100% taste experience (liquid B) or a mixture of both.

In this embodiment, the inhaler housing 68 has two housing parts 74, 75, which are detachably connected to one another for the consumer and which, in the separated state, allows the cartridge 19 to be inserted or reversibly inserted into one of the two housing parts 74, 75, wherein the electrical contact elements 7, 22 come into operative connection with one another in order to establish the electrical connection of the evaporator unit 23 in the cartridge 19 to the base part 20.

An indicator 76 of the charge level of the energy store 76 in the inhaler and/or an indicator of the remaining amount of liquid in the reservoir (s) 37A, 37B, . . . of the inhaler 27 is advantageously provided on the outside of the housing 68 and thus visible to the consumer.

In order to trigger a vapour boost, i.e. a briefly increased amount of vapour and/or active substance, the housing 68 of the inhaler 27 advantageously has a boost actuator 30, for example a push button, which can be actuated by the consumer. As a result of the actuation of the boost actuator 30, the electronic control device 56 controls the evaporator device 1 in order to generate an increased amount of vapour and/or active substance for a predefined period. This can happen, for example, by increasing the evaporation power of the evaporators 3 and/or by simultaneously triggering several or all of the evaporators 3. The power of the evaporators 3 is advantageously set via pulse width modulation.

Figure 10:
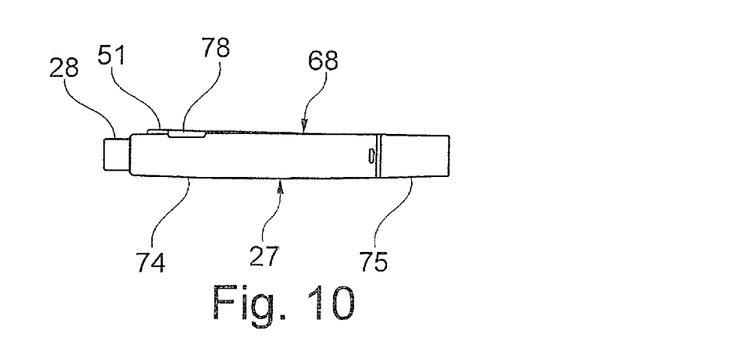
FIG. 10 is a side view of a rod-shaped electronic cigarette product in a further embodiment.
Figure 11:
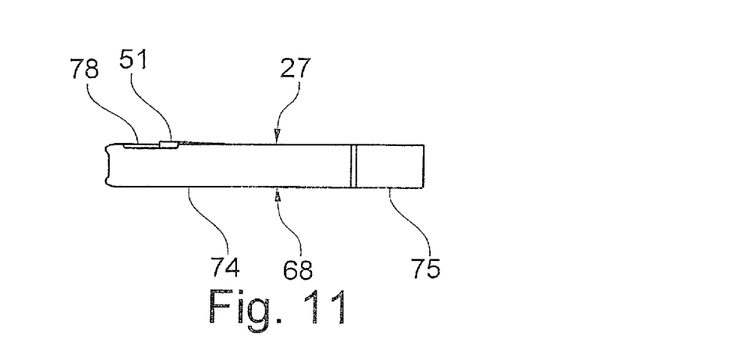
FIG. 11 is a side view of the rod-shaped electronic cigarette product according to FIG. 10 having the mouthpiece inserted.

An embodiment of a rod-shaped e-cigarette 27 having an adjustable mouthpiece 28 is shown in FIGS. 10 and 11. The mouthpiece 28 is advantageously arranged to be displaceable by the consumer along the longitudinal axis of the rod-shaped e-cigarette 27 between the end positions shown in FIGS. 10 and 11, in particular by means of a mechanical actuating element 51. The housing 68 advantageously has a groove 78 which is arranged parallel to the longitudinal axis of the rod-shaped e-cigarette 27 and in which the actuating element 51 is displaceably guided.

In the position shown in FIG. 10, the mouthpiece 29 is fully moved out of the inhaler housing 68, such that the e-cigarette 27 is ready for operation.

In the position shown in FIG. 11, the mouthpiece 28 has been moved into the inhaler housing 68 and is completely lowered therein. This ensures hygienic protection of the mouthpiece 28 when the e-cigarette 27 is in the unoperated state. The inhaler 27 is advantageously switched off by adjusting the state shown in FIG. 11 by means of the actuating element 51, i.e. the supply of energy from the energy store 46 is interrupted. The inhaler 27 is also advantageously switched on by adjusting the state shown in FIG.

10 by means of the actuating element 51. The actuating element 51 then simultaneously serves as an on-off switch, such that a separate on-off switch is unnecessary.

It is also advantageously possible that the actuating element 51 can assume intermediate states between the end positions shown in FIGS. 10 and 11, in order in this way to be able to adjust the puff resistance of the inhaler 27 and/or the amount of vapour and/or the active substance content. A separate switch 73 as in FIGS. 4 and 5 can then be dispensed with.

Figure 12:
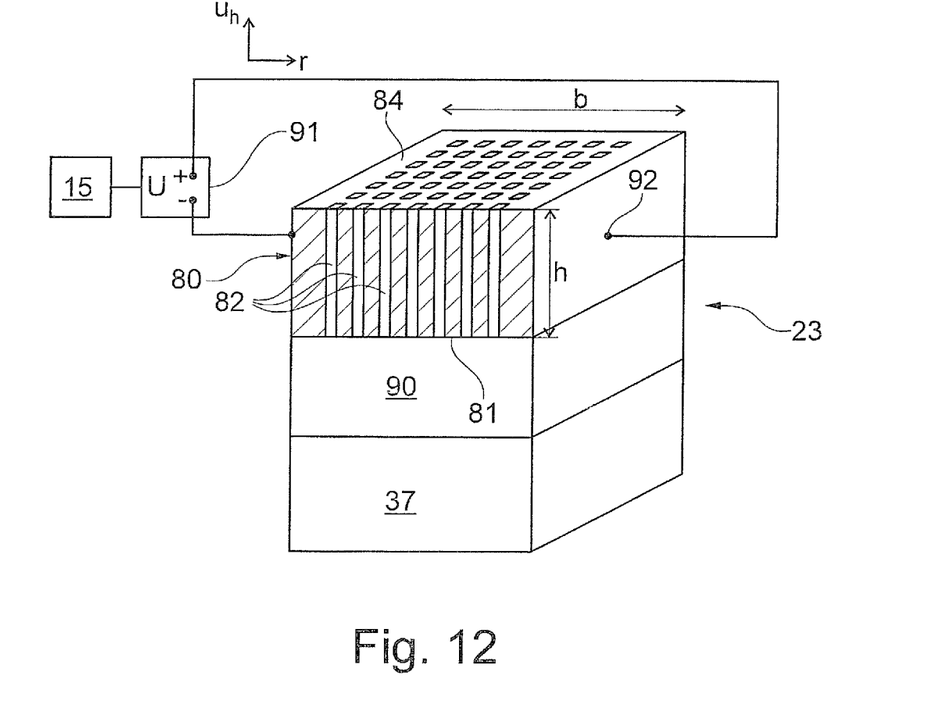
FIG. 12 is a schematic cross-sectional view of an exemplary evaporator unit for an e-cigarette.

An advantageous embodiment of an evaporator 3 according to the invention is shown in FIG. 12. The evaporator 3 is here formed by a block-shaped, advantageously monolithic heating element 80, preferably made of an electrically conductive material, preferably silicon, doped ceramic, metal ceramic, filter ceramic, semiconductor, in particular germanium, graphite, semimetal, and/or metal. It is not necessary for the entire heating element 80 to be made of an electrically conductive material. It may be sufficient, for example, that the surface of the heating body 80 is coated in an electrically conductive manner, for example has a metallic coating. In this case, the entire surface does not have to be coated; for example, conductor tracks can be provided on a non-conductive base body.

The heating element 80 is provided with a plurality of microchannels 82, which connect an inlet side 81 of the heating element 80 to an outlet side 84 in a liquid-conducting manner. The inlet side 81 is connected, for example, to the liquid store 37 in a liquid-conducting manner via a wick structure 90. The wick structure 90 is used for the passive conveyance of liquid from the liquid store 37 to the heating element 80 by means of capillary forces. The wick structure 90 in the contact region 81 to the heating element 80 serves to distribute liquid evenly, to be temperature-resistant and to form a kind of check valve with its relatively small pores and/or thin capillaries in order to prevent undesirable backflow of bubbly liquid from the heating element 80 into the wick structure 90 and/or into the liquid store 37.

Instead of the wick structure 90, other passive and/or active conveying devices can be provided for conveying liquid from the liquid store 37 to the heating element 80.

The median diameter of the microchannels 82 is preferably in the range between 5 µm and 200 µm, more preferably in the range between 30 µm and 150 µm, even more preferably in the range between 50 µm and 100 µm. Due to these dimensions, a capillary effect is advantageously produced, so that liquid penetrating into a microchannel 82 at the inlet side 81 rises upwards through the microchannel 82 until the microchannel 82 is filled with liquid. The volume ratio of the microchannels 82 to the heating element 80, which can be referred to as the porosity of the heating element 80, is for example in the range between 10% and 50%, advantageously in the range between 15% and 40%, more advantageously in the range between 20% and 30%, and is, for example, 25%.

The edge lengths of the surfaces of the heating element 80 provided with microchannels 82, for example, are in the range between 0.5 mm and 3 mm. For example, the dimensions of the surfaces of the heating element 80 provided with microchannels 82 can be as follows: 0.95 mm×1.75 mm; 1.9 mm×1.75 mm or 1.9 mm×0.75 mm. The edge lengths of the heating element 80 can be, for example, in the range between 0.5 mm and 5 mm, preferably in the range between 0.75 mm and 4 mm, more preferably in the range between 1 mm and 3 mm. The surface of the heating element 80 (chip size), for example, can be 1 mm×3 mm or 2 mm×3 mm.

The width b of the heating element 80 is preferably in the range between 1 mm and 5 mm, more preferably in the range between 2 mm and 4 mm, and is, for example, 3 mm. The height h of the heating element 80 is preferably in the range between 0.05 mm and 1 mm, more preferably in the range between 0.1 mm and 0.75 mm, even more preferably in the range between 0.2 mm and 0.5 mm, and is, for example, 0.3 mm.

The number of microchannels 82 is preferably in the range between four and 1000. This allows the heat input from the carrier into the microchannels 82 to be optimised and ensures a high evaporation capacity and a sufficiently large vapour outlet surface.

The microchannels 82 are advantageously arranged in the form of a square, rectangular, polygonal, round, oval or differently shaped array. The array may be in the form of a matrix having s columns and z rows, wherein s is advantageously in the range between 2 and 50 and more advantageously in the range between 3 and 30 and/or z is advantageously in the range between 2 and 50 and more advantageously in the range between 3 and 30. This allows for an effective and easily manufactured arrangement of microchannels 82 having a guaranteed high evaporation capacity.

The cross section of the microchannels 82 can be square, rectangular, polygonal, round, oval or otherwise shaped and/or can vary lengthwise in portions, in particular may increase, decrease or remain constant.

The length of one or each microchannel 82 is preferably in the range between 100 µm and 1000 µm, more preferably in the range between 150 µm and 750 µm, even more preferably in the range between 180 µm and 500 µm, and is, for example, 300 µm. In this way, optimal liquid absorption and portion formation with sufficiently good heat input from the radiator 80 into the microchannels 82 can be achieved.

The distance between two microchannels 82 is preferably at least 1.3 times the clear diameter of one microchannel 82, wherein the distance refers to the centre axes of the two microchannels 82. The distance can preferably be 1.5 to 5 times the clear diameter of a microchannel 82, more preferably 2 to 4 times. In this way, an optimal heat input from the carrier into the microchannels and a sufficiently stable arrangement and wall thickness of the microchannels can be realised.

The evaporator unit 20 has a heating voltage source 91, preferably controllable by the control device 56, which is connected via electrodes 92 to opposite sides of the heating element 80, in such a manner that an electrical voltage Uh produced by the heating voltage source 91 leads to a current flow through the heating element 80. Due to the ohmic resistance of the electrically conductive heating element 80, the current flow leads to heating of the heating element 80 and therefore to evaporation of the liquid contained in the microchannels 82. The heating element 80 thus acts as an evaporator 3.

The duration of the individual evaporation steps at different temperatures and/or an evaporation of the individual components of the individual portions of the liquid can be kept so short and/or clocked using an trigger frequency that the step-by-step evaporation cannot be perceived by a consumer and nevertheless a largely homogeneous, repeatable, precise aerosol formation having good taste conformity can be ensured. In particular, it is advantageous to first evaporate a low-boiling component of the liquid in a first evaporation interval at a first temperature A, and then to evaporate a high-boiling component of the liquid in a second evaporation interval at a second temperature B, which exceeds the temperature A.

The trigger frequency of the heating element 80 produced by the heating voltage source 91 is advantageously in the range from 1 Hz to 50 kHz, preferably in the range from 30 Hz to 30 kHz, and even more advantageously in the range from 100 Hz to 25 kHz.

The course of the evaporation procedure is explained below.

In an initial state, the voltage source 91 for the heating procedure is switched off.

To evaporate liquid, the voltage source 91 for the heating element 80 is activated. The voltage Uh is set in such a manner that the evaporation temperature in the heating element 80 and therefore in the microchannels 82 is adapted to the individual evaporation behaviour of the liquid mixture used. This prevents the danger of local overheating and thereby the formation of harmful substances.

As soon as a quantity of liquid equal to or related to the volume of the microchannels 82 has evaporated, the heating voltage source 91 is deactivated. Since the liquid properties and amount are advantageously known exactly, this point in time can be controlled very precisely. The energy consumption of the evaporator unit 23 can therefore be reduced compared to known devices, since the required evaporation energy can be metered and thereby introduced more precisely.

After completion of the heating procedure, the microchannels 82 are predominantly or completely emptied. The heating voltage 91 is then kept switched off until the microchannels 82 are replenished by feeding liquid through the wick structure 90. When this happens, the next heating cycle can be started by switching on the heating voltage 91.

The heating element 80 is preferably produced on the basis of MEMS technology, in particular from silicon, and is therefore advantageously a micro-electromechanical system.

Embodiments

Embodiment 1. Inhaler (27), in particular electronic cigarette product, comprising at least one evaporator unit (23) with at least one electric evaporator (3) for evaporating liquid supplied to the evaporator (3), and comprising an electronic controller (56) for controlling and/or regulating the at least one evaporator unit (23), characterised in that the inhaler (27) has at least one replaceable cartridge (19), wherein the cartridge (19) has the evaporator unit (23) and a liquid tank (6) which is connected or can be connected.

Embodiment 2. Inhaler according to embodiment 1, characterised in that the at least one cartridge (19) forms a plurality of reservoirs (37A, 37B, . . .) for storing a plurality of liquids.

Embodiment 3. Inhaler according to embodiment 2, characterised in that the inhaler (27) has an actuatable selection element (70) for selecting a reservoir from which liquid is to be evaporated, from the plurality of reservoirs (37A, 37B, . . .).

Embodiment 4. Inhaler according to embodiment 3, characterised in that the selection element (70) is a push button, wherein the plurality of reservoirs (37A, 37B, . . .) are sequentially run through by repeated actuation of the push button.

Embodiment 5. Inhaler according to either embodiment 3 or embodiment 4, characterised in that the inhaler (27) has an indicator (72) which informs the consumer about the selected reservoir (37A, 37B, . . .) and/or about the liquid contained therein.

Embodiment 6. Inhaler according to embodiment 5, characterised in that the indicator (72) is set up to display a characteristic of the selected liquid, in particular flavour, active ingredient content and/or vapour formation potential.

Embodiment 7. Inhaler according to embodiment 6, characterised in that the indicator (72) shows the characteristic of the selected liquid by means of a colour coding.

Embodiment 8. Inhaler according to any of the preceding embodiments, characterised in that the inhaler (27) has a head (25) in which the cartridge or all of the cartridges (19) is/are arranged.

Embodiment 9. Inhaler according to embodiment 8, wherein the inhaler (27) has an energy store (46), characterised in that the energy store (46) is arranged entirely or in part in the head (25)

Embodiment 10. Inhaler according to either embodiment 8 or embodiment 9, characterised in that the inhaler (27) has a mouthpiece (28) and a puff tube (59) connecting the mouthpiece (28) to the head (25).

Embodiment 11. Inhaler according to embodiment 10, characterised in that the length Ls of the puff tube (59) is greater than the length Lk of the head (25).

Embodiment 12. Inhaler according to any of the preceding embodiments, characterised in that the inhaler (27) has a reversibly removable cover (61) for closing an opening in a housing (68) of the inhaler (27) through which the at least one cartridge (19) can be inserted into the inhaler (27) and removed therefrom.

Embodiment 13. Inhaler according to embodiment 12, characterised in that the cover (61) is held on the housing (68) of the inhaler (27) by means of magnets.

Embodiment 14. Inhaler according to either embodiment 12 or embodiment 13, characterised in that the cover (61) has at least one receptacle (62) for receiving the at least one cartridge (19), and at least one electrical contact element (22) for interacting with a corresponding electrical contact element (7) of the at least one cartridge (19).

Embodiment 15. Inhaler according to embodiment 14, characterised in that the cover (61) has an electrical contact element (65) which is connected to the electrical contact element (22) and is set up to interact with a corresponding contact element arranged on a base part (20) of the inhaler (27) in order to establish an electrical connection between the at least one cartridge (19) and the base part (20).

Embodiment 16. Inhaler according to any of the preceding embodiments, characterised in that the inhaler (27) has a switch (73) for setting different operating variables of the inhaler (27).

Embodiment 17. Inhaler according to embodiment 16, characterised in that the switch (73) is set up to adjust the amount of vapour to be generated per puff.

Embodiment 18. Inhaler according to either embodiment 16 or embodiment 17, characterised in that the switch (73) is set up to adjust the puff resistance of the inhaler (27).

Embodiment 19. Inhaler according to any of embodiments 16 to 18, characterised in that the switch (73) serves as an on-off switch for the inhaler (27).

Embodiment 20. Inhaler according to any of the preceding embodiments, characterised in that the inhaler (27) has an inductive charging interface (42) for inductively charging the energy store (46).

Embodiment 21. Inhaler according to any of the preceding embodiments, characterised in that the inhaler (27) has an actuating element (30) for triggering a briefly increased amount of vapour and/or active ingredient.

Embodiment 22. Inhaler according to any of the preceding embodiments having a mouthpiece (28), characterised in that the mouthpiece (28) is adjustable, in particular displaceable, between a lowered position and an extended operating position by means of an actuating element (51).

Embodiment 23. Inhaler according to embodiment 22, characterised in that the inhaler (27) is switched off by moving the mouthpiece (28) into the lowered position and the inhaler (27) is switched on by moving the mouthpiece (28) into the extended position.

Embodiment 24. Inhaler according to either embodiment 22 or embodiment 23, characterised in that by adjusting the mouthpiece (28) the puff resistance of the inhaler (27) is changed at the same time.

The invention claimed is:

1. An inhaler, comprising:
    at least one evaporator unit with at least one electric evaporator for evaporating liquid supplied to the electric evaporator;
    an electronic controller for controlling and/or regulating the at least one electric evaporator unit;
    at least one replaceable cartridge, wherein the at least one replaceable cartridge has the at least one electric evaporator unit and a liquid tank which is connectable;
    a housing;
    a reversibly removable cover for closing an opening in the housing through which the at least one replaceable cartridge is insertable into the inhaler and removable therefrom,
    wherein the at least one replaceable cartridge forms a plurality of reservoirs for storing a plurality of liquids; and
    an actuatable selection element for selecting a reservoir of the plurality of reservoirs from which liquid is to be evaporated.

2. The inhaler according to claim 1, wherein the actuatable selection element is a push button, wherein the plurality of reservoirs are sequentially run through by repeated actuation of the push button.

3. The inhaler according claim 1, further comprising:
    an indicator which informs a consumer about the selected reservoir of the plurality of reservoirs and/or about a liquid of the plurality of liquids contained therein.

4. The inhaler according to claim 3, wherein the indicator is set up to display a characteristic of the liquid of the plurality of liquids, wherein the characteristic is one or more of the following: flavour, active ingredient content, and vapour formation potential.

5. The inhaler according to claim 4, wherein the indicator shows the characteristic of the liquid of the plurality of liquids via colour coding.

6. The inhaler according to claim 1, further comprising:
    a head in which one or more of the at least one replaceable cartridge is arranged.

7. The inhaler according to claim 6, further comprising:
    an energy store, wherein the energy store is arranged entirely, or in part, in the head.

8. The inhaler according to claim 6, further comprising:
    a mouthpiece; and
    a puff tube connecting the mouthpiece to the head.

9. The inhaler according to claim 8, wherein a length Ls of the puff tube is greater than a length Lk of the head.

10. The inhaler according to claim 1, wherein the reversibly removable cover is held on the housing via magnets.

11. An inhaler, comprising:
    at least one evaporator unit with at least one electric evaporator for evaporating liquid supplied to the electric evaporator;
    an electronic controller for controlling and/or regulating the at least one electric evaporator unit;
    at least one replaceable cartridge, wherein the at least one replaceable cartridge has the at least one electric evaporator unit and a liquid tank which is connectable;
    a housing; and
    a reversibly removable cover for closing an opening in the housing through which the at least one replaceable cartridge is insertable into the inhaler and removable therefrom,
    wherein the reversibly removable cover has at least one receptacle for receiving the at least one replaceable cartridge, and at least one electrical contact element for interacting with a corresponding electrical contact element of the at least one replaceable cartridge.

12. The inhaler according to claim 11, wherein the reversibly removable cover has an electrical contact element which is connected to the electrical contact element and is set up to interact with a corresponding contact element arranged on a base part of the inhaler in order to establish an electrical connection between the at least one replaceable cartridge and a base part.

13. The inhaler according to claim 1, further comprising:
    a switch for setting different operating variables of the inhaler.

14. The inhaler according to claim 13, wherein the switch is set up to adjust an amount of vapour to be generated per puff.

15. The inhaler according to claim 13, wherein the switch is set up to adjust a puff resistance of the inhaler.

16. The inhaler according to claim 13, wherein the switch serves as an on-off switch for the inhaler.

17. The inhaler according to claim 1, further comprising:
    an inductive charging interface for inductively charging the energy store.

18. The inhaler according to claim 1, further comprising:
    an actuating element for triggering a briefly increased amount of vapour and/or active ingredient.

\* \* \* \* \*